United States Patent
Ruschhaupt

(10) Patent No.: US 11,871,770 B1
(45) Date of Patent: Jan. 16, 2024

(54) SWEETENER ADDITIVE FOR FOOD AND DRINK PRODUCTS TO IMPROVE HEALTH AND WELL-BEING

(71) Applicant: RB2 Enterprises, LLC, San Diego, CA (US)

(72) Inventor: Ryan Ruschhaupt, Lake Almanor, CA (US)

(73) Assignee: RB2 Enterprises, LLC, San Diego, CA (US)

( * ) Notice: Subject to any disclaimer, the term of this patent is extended or adjusted under 35 U.S.C. 154(b) by 210 days.

(21) Appl. No.: 17/159,108

(22) Filed: Jan. 26, 2021

(51) Int. Cl.
| | |
|---|---|
| *A61K 36/738* | (2006.01) |
| *A23L 27/30* | (2016.01) |
| *A23L 33/18* | (2016.01) |
| *C12N 9/02* | (2006.01) |
| *C12N 9/04* | (2006.01) |
| *A23L 33/00* | (2016.01) |

(52) U.S. Cl.
CPC ............. *A23L 27/33* (2016.08); *A23L 27/31* (2016.08); *A23L 33/18* (2016.08); *A23L 33/30* (2016.08); *C12N 9/0006* (2013.01); *C12N 9/0008* (2013.01)

(58) Field of Classification Search
CPC .......... A23L 27/33; A23L 27/31; A23L 33/18; A23L 33/30; C12N 9/0006; C12N 9/0008
USPC ......................................................... 426/548
See application file for complete search history.

(56) References Cited

U.S. PATENT DOCUMENTS

| | | | |
|---|---|---|---|
| 2011/0280977 A1* | 11/2011 | Park ................... | A61P 43/00 424/765 |
| 2022/0347153 A1* | 11/2022 | Ruschhaupt ......... | A61K 8/9789 |

OTHER PUBLICATIONS

Meng et al., Evaluation of Total Flavonoids, Myricetin, and Quercetin from Hovenia dulcis Thunb. As Inhibitors of α-Amylase and a-Glucosidase, Plant Foods Hum Nutr (2016) 71:444-449. (Year: 2016).*

* cited by examiner

*Primary Examiner* — Brent T O'Hern
(74) *Attorney, Agent, or Firm* — Richard A. Ryan

(57) ABSTRACT

A sweetener additive for use with consumable products, such as foods and beverages, to sweeten the consumable product and provide health benefits to a consumer who consumes a consumable product. The sweetener additive has a sweetener base and one or more of selected flavonoids. The sweetener base has one or more sweeteners commonly utilized to sweeten consumable products. The flavonoids may be extracted from plants chosen from the genus *Hovenia*, such as the Japanese raisin tree. The selected flavonoids provide various health benefits, including stimulating naturally occurring enzymes in the consumer's body. One or more aldehyde reducing enzymes, one or more glucose reducing enzymes and/or one or more alcohol reducing enzymes may be added to the sweetener additive to supplement naturally occurring enzymes in the consumer's body to reduce the deleterious effects of aldehydes, glucose and/or alcohol on the consumer. The flavonoids will also stimulate the added enzymes.

20 Claims, 2 Drawing Sheets

SWEETENER ADDITIVE FOR FOOD AND DRINK PRODUCTS TO IMPROVE HEALTH AND WELL-BEING

CROSS-REFERENCE TO RELATED APPLICATIONS

None.

STATEMENT REGARDING FEDERALLY SPONSORED RESEARCH

Not Applicable.

REFERENCE TO A SEQUENCE LISTING, A TABLE OR A COMPUTER PROGRAM LISTING APPENDIX SUBMITTED ON A COMPACT DISC

Not Applicable.

BACKGROUND OF THE INVENTION

A. Field of the Invention

The present invention relates generally to sweeteners that are added to food and drink products to make the food and drink products more tasteful and enjoyable. In particular, the present invention relates to such sweeteners that are utilized as an additive which are added to food and drinks during the manufacturing thereof or which may be added by the consumer prior to his or her consumption of a food or drink product. Even more particularly, the present invention relates to such sweetener additives that comprise specific components which help mitigate the otherwise harmful effects of prior art sweeteners and that provide other health benefits to the person consuming a food or drink product having the sweetener additive.

B. Background

A wide variety of different types of foods and drinks are consumed by people throughout the world. Although many people attempt to consume healthy foods and drinks, even to go as far as to limit their diet to only or at least primarily organic fruits and vegetables and naturally grown or harvested meat, the reality is that the food and drink diet of most people is not that healthy. Specifically, the vast majority of people consume food that is high in sugar, fat, carbohydrates and other components that are not healthy when consumed in the quantities that most people consume these components. With regard to sugar and other sweeteners, including a wide variety of artificial sweeteners, the consumption and over-consumption of foods and drinks with sugar contributes significantly to people being considered generally unhealthy. For purposes of describing the present invention, foods and drinks that are consumed, whether or not they contain or may contain sugar or any other harmful ingredients, are collectively referred to as "consumable products". Although the present invention primarily discusses consumable products in terms of the consumption and the effects of the consumption of consumable products by humans, the term is also used to refer to animal food, particularly pet food, that is intended to be consumed by animals. Likewise, the term "sweetener" refers to any sweetener-type components that are added to or utilized with any consumable product, whether the sweetener is added to the consumable product during the production thereof (i.e., cooking, baking, frying, mixing or other means of making the consumable product) or added by a person, whether or not he or she is the person who will consume the consumable product, prior to or while consuming the consumable product. In addition, the term "sweetener" refers to any type of component that is added to a consumable product, typically but not exclusively to make it sweeter or otherwise more desirable for consumption, by the person who is or will be consuming the consumable product. Although various examples of consumable products and sweeteners are described herein, the listing of such examples is provided for exemplary purposes only and, as such, is not intended to limit the present invention to just those examples.

The human consumption of sweeteners in consumable products is well known to be a health issue for people of all ages and is considered by some people in the United States health or medical fields to be a national health issue. In fact some schools and certain geographical locations, including cities, towns and other municipalities, have gone as far as to ban or substantially limit the availability of consumable products with artificially added sweeteners (as opposed to those consumable products having natural sweeteners, such as fruits, fruit juice and the like). In a typical American diet, the top sources of sugar and other sweeteners are soft drinks, fruit drinks, flavored yogurt, cereals, cookies, cakes, candy and most processed foods. Unfortunately, added sugar or other sweeteners is also present in consumable products that are generally not considered be sweetened, including such foods as soup, bread, cured meat, and ketchup. Despite the known problems associated with the consumption, particularly the over-consumption of consumable products with sweeteners, people generally prefer such consumable products because the sweeteners are known to, at least for most people, somewhat improve the taste and, typically, the enjoyableness of the consumable product.

The health problems associated with sweeteners in general, and with sugar specifically, are commonly known to include such problems as obesity, cavities and diabetes. With regard to obesity, the increase in weight due to the consumption of added sugar and other sweeteners, particularly in sweetened beverages, is a well documented problem. Sweetened drinks like sodas, juices and sweet teas are loaded with fructose, a type of simple sugar. Studies have shown that consuming fructose increases a person's hunger and desire for food, even more than consuming glucose, the main type of sugar found in starchy foods. In addition, there is a belief that excessive fructose consumption can result in a resistance to leptin, which is an important hormone that regulates hunger and tells your body to stop eating, meaning that sweetened beverages tend to increase a person's hunger instead of curbing hunger. With regard to cavities, eating too much sweetened consumable products often results in cavities because bacteria in a person's mouth will feed on the sweetener and release acid byproducts that can cause tooth demineralization. Studies have also shown there is a direct and clear link between excessive sweetener consumption and diabetes risk. Besides the fact that obesity is generally considered the strongest risk factor for diabetes, prolonged sweetener consumption can lead to a resistance to insulin, which is a hormone that is produced by the pancreas to regulates blood sugar levels, that can cause blood sugar levels to rise and strongly increases the risk of diabetes.

As well known to persons who are skilled in the art, the above health impacts are not the only problems associated with consumption of consumable products with sweeteners. For instance, the consumption of sweeteners is also known to contribute to heart disease. Studies have shown an association between a high-sugar diet and a greater risk of dying from heart disease, in part due to the increase likelihood of obesity. In one possible pathway, the consumption of high amounts of sugar and other sweeteners overloads the liver, which metabolizes sugar the same way as alcohol and converts dietary carbohydrates to fat that, over time, can lead to a greater accumulation of fat in the liver (i.e., fatty liver disease) which can contribute to diabetes and raise a person's risk for heart disease. In addition, consuming too much added sweeteners can raise a person's blood pressure and increase chronic inflammation, both of which are pathological pathways to heart disease and stroke. Studies have also shown that consuming too much consumable products having sugar and other sweeteners can lead to an increased risk of certain types of cancers due, in part, to causing inflammation in the body and insulin resistance. For instance, such consumption is associated with an increased risk of esophageal cancer, pleural cancer, cancer of the small intestine and endometrial cancer. A diet that is high in processed foods having added sugar or other sweeteners has also been shown to increase a person's chances of developing depression and other mental health due to blood sugar swings, neurotransmitter dysregulation and inflammation. Studies have also shown that consuming high-sugar diets can accelerate cognitive decline, including impaired memory and an increased risk of dementia. Having consistently high blood sugar levels, which can result from consumption of consumable products with sweeteners, can damage the blood vessels in the kidneys, which can lead to an increased risk of kidney disease. Excessive consumption of consumable foods with sweeteners can raise uric acid levels in a person's blood, increasing the risk of developing or worsening gout. The consumption of consumable products having sweeteners can speed the skin aging process, worsen wrinkles and contribute to acne.

One example of consuming sweetener is the consumption of alcohol. Although many people enjoy consuming alcohol products, including beer, spirits, wine, mixed drinks, wine coolers and the like, the over-consumption of alcohol, and in some circumstances even consumption of relatively small amounts of alcohol, has resulted in a wide variety of problems for society. For purposes of describing the various aspects and benefits of the present invention, the terms "alcohol" and "alcohol beverages" are utilized herein to include wine, beer, distilled spirits, malt liquors and other drinks that contain wine, beer or distilled spirits with one or mixers (such as fruit juice, soda, seltzer and the like).

It is well known that consuming alcohol often has serious negative affects for the person, some of which are long term and some of which can last for hours or even one or more days after the alcohol has been consumed. Long term effects of the over-consumption of alcohol (i.e., alcohol abuse and dependence) include a number of physical, social and psychological problems, including acute alcohol poisoning, fetal alcohol syndrome and cirrhosis of the liver. The short term effects resulting from the over-consumption of alcohol, which effects are commonly referred to has a "hangover", include symptoms such as a headache, body ache, fatigue, upset stomach (i.e., nausea), and the like. As generally well known, many hangover symptoms are caused by an accumulation of acetaldehyde in a person's bloodstream due to the inability of his or her liver to process alcohol consumed by the person quickly enough. Although the symptoms of a hangover usually only last for relatively short amount of time, depending on the amount of alcohol a person has consumed, the person's individual tolerance to alcohol and the amount of different types of food and liquids consumed prior to drinking, these hangover symptoms can be somewhat severe and even generally debilitating. At the very least, such symptoms can be unpleasant, inconvenient and negatively impact the person's ability to be able to function normally at home and work, which will affect his or her productivity.

As well known by persons who are skilled in the art, acetaldehyde, as well as other aldehydes (of which acetaldehyde is one type of aldehyde), also will accumulate in a person's bloodstream from sources other than the consumption of alcohol. For instance acetaldehyde, which is a carcinogen that causes cancer and a wide range of other health problems, contamination of the bloodstream can be caused by environmental pollution, eating too much sugar or sugary foods and/or vaping or smoking cigarettes and *cannabis*. While the amount of aldehyde in a person's bloodstream causing problems for a person (e.g., hangover effects) may be most commonly associated with the consumption of alcohol, particularly over-consumption of alcohol, the aldehyde accumulation in a person's bloodstream from other sources will have an amplifying effect on a person who consumes alcohol with regard to making his or her hangover symptoms worse. In addition, some people are genetically disposed so as to not be able to process acetaldehyde and other aldehydes very well, which of course will make aldehyde accumulation from alcohol and other sources much more of a problem with regard to hangover and hangover-type symptoms for him or her and with regard to processing the carcinogen in a safe and effective manner. Some people have an unhealthy liver, whether genetically or due to prior alcohol problems, that creates problems with processing acetaldehyde and other aldehydes in a manner which lowers and, preferably, removes these carcinogen from the person's bloodstream.

As well known in the art, people have enzymes in their body which act on aldehydes, including acetaldehyde, in the blood stream to reduce the amount of the aldehyde accumulation in a person's bloodstream, whether the accumulation is from alcohol, environmental conditions, eating habits, work or liver problems. Two such enzymes are alcohol dehydrogenase and aldehyde dehydrogenase. While these two enzymes do, over time, reduce the amount of aldehyde in a person's bloodstream, the introduction of alcohol and other sources of aldehydes can easily overwhelm the ability of these enzymes to efficiently, effectively and quickly reduce aldehydes in a person's bloodstream. Activating or supplementing these enzymes could help the person's body eliminate aldehydes, including acetaldehyde, in his or her bloodstream.

As will be appreciated by persons who are skilled in the art, it would be beneficial to have a sweetener for use in or with consumable products which helps counteract the negative effects of consuming the sweetener. It would also be very beneficial to have a sweetener that is suitable for use in or with a consumable product which has the effect of improving the overall health and well-being of the person who consumes the consumable product instead of causing the problems that are presently associated with sweeteners (as described above). What is needed, therefore, is a sweetener additive that can be added to a consumable product to help a person's body mitigate the otherwise harmful effects of the sweetener and to improve the person's overall health and well being. More specifically, what is needed is a sweetener additive that assists the body of a person who consumes a consumable product having the sweetener additive to process the sweetener in a healthier manner and to provide additional health benefits, including reducing the amount of acetaldehyde and other aldehydes in his or her bloodstream, whether the aldehydes are from drinking alcohol, environment, smoking, sugar consumption or other reasons. The new sweetener additive should be able to stimulate and help produce additional enzymes in a person's body that will allow him or her to better process the sweetener and to reduce the amount of acetaldehyde and other aldehydes in his or her bloodstream. The new sweetener additive should be adaptable for use in the production of consumable foods and for use on consumable foods prior to consuming the consumable foods, such as adding the sweetener additive to a food or beverage prior to eating the food or drinking the beverage. Preferably, the new sweetener additive should be relatively inexpensive to manufacture so it can be widely utilized.

SUMMARY OF THE INVENTION

The following presents a simplified summary of the disclosure of the present invention in order to provide a basic understanding of the invention to the reader. As such, this Summary is not an extensive overview of the disclosure and it does not identify key/critical elements of the invention or delineate the scope of the invention. The sole purpose of this Summary is to present some concepts disclosed herein in a simplified form as a prelude to the more detailed description that is presented later.

The use of terms such as "including", "comprising" or "having" and variations thereof herein is meant to encompass the items listed thereafter and equivalents thereof. The terms "a" and "an" herein do not denote a limitation of quantity, but rather denote the presence of at least one of the referenced item. Further, the use of terms "first", "second", and "third", and the like, herein do not denote any order, quantity, or importance, but rather are used to distinguish one element or feature of an element from another. The term "and/or," when used herein with a list of two or more items, means that any one of the listed items can be employed by itself, or any combination of two or more of the listed items can be employed.

The present invention provides the benefits and solves the problems which are identified above. That is to say, the present invention is directed to a new sweetener additive that is added to a consumable product to help a person's body mitigate the otherwise harmful effects of the sweetener itself and to improve the person's overall health and well being. More specifically, the present invention is a sweetener additive that, when added to a consumable product and consumed by a person (i.e., a consumer of the consumable product), assists the consumer by enabling his or her body to process the sweetener in a healthier manner and to provide additional health benefits, including reducing the amount of acetaldehyde and other aldehydes in his or her bloodstream, whether the aldehydes are from drinking alcohol, environment, smoking, sugar consumption or other reasons. The sweetener additive of the present invention comprises a sweetener base selected from one or more presently available sweeteners, such as sugar and the like, and one or more flavonoids mixed with the sweetener base, with the flavonoids derived from plants in the plant genus *Hovenia*. In addition to sweetening the consumable product with which it is utilized, the new sweetener additive stimulates enzymes and helps produce additional enzymes in a person's body that will allow him or her to better and in a more healthier manner process the sweetener and reduce the amount of acetaldehyde and other aldehydes in his or her bloodstream.

As such, in addition to making a consumable product more enjoyable to consume and his or her body better able to process the sweetener, the new sweetener additive also provides significant health benefits to the person consuming a consumable product having the sweetener added to the consumable product. The new sweetener additive of the present invention can be used in the production of consumable foods and for use by the consumer on a consumable food prior to when he or she consumes the consumable food, such as adding the sweetener additive to a food or beverage prior to eating the food or drinking the beverage. In the preferred embodiments, the new sweetener additive is relatively inexpensive to manufacture so it will be able to be widely utilized.

The one or more healthy flavonoids in the new sweetener additive are able to stimulate naturally occurring enzymes in the consumer's body that aide in the conversion of ethanol and glucose prior to these substances being released and stored in the consumer's body. In addition, to supporting the healthy removal and regulation of sugars in the body, the flavonoids in the new sweetener additive also stimulate and produce enzymes that help the consumer's body process and remove carcinogenic toxins called aldehydes that are caused by excessive sugar intake, alcohol consumption, smoking, vaping, pollution, and/or poor diet. As is well known in the art, the accumulation of aldehydes in the body is a major cause of cancer, liver disease, brain fog and hangover. The addition of flavonoids in the new sweetener additive of the present invention actively supports healthier liver, organ and brain function as an additive contained in a consumable product. By utilizing the new sweetener additive with consumable products, the consumer will make his or her life more healthy, fun, entertaining and enjoyable by reducing the harmful effects of consuming consumable products that are produced with the new sweetener additive or which have the sweetener additive added thereto prior to the consumer consuming the consumable product.

In one embodiment of the present invention, the new sweetener additive generally comprises a sweetener base and one or more flavonoids that are selected from the group comprising at least one of Apigenin, Flavanones, Kaempferol, Quercetin, Rutin, Myricetin, Dihdrokaempferol, Dihydromyricetin, Ampelopsin, Epigallocatechin gallate and Taxifolin. The flavonoids are combined with the sweetener base for use with a consumable product to provide one or more health benefits for the consumer who consumes the consumable product having the sweetener additive so as to improve the health and well-being of the consumer. The sweetener base has one or more sweeteners. In one embodiment, the flavonoids are selected from plants in the plant genus *Hovenia*. The one or more flavonoids are combined with the sweetener base to produce the sweetener additive. The sweetener additive, which may be in a powder, liquid, granular or other form, is added to the consumable product during production of the consumable product and/or it is added to the consumable product after production of the consumable product but before the consumer eats or drinks the consumable product. The consumable product can be a food, beverage or a mix to make a food or beverage. In one embodiment, the sweeteners of the sweetener base comprises at least one of a cane sugar, an other plant sugar, a syrup sugar, an artificial sugar and an other sugar that are selected to, at least generally, sweeten or otherwise benefit the taste, texture or other features of the consumable product. In another embodiment, the sweetener additive can have an aldehyde reducing component that is selected to supplement naturally occurring enzymes in the consumer's body in a manner which reduces the deleterious effects of aldehydes on the consumer. The aldehyde reducing component can comprise an aldehyde dehydrogenase enzyme. In another embodiment, the sweetener additive can have a glucose reducing component that is selected to supplement naturally occurring enzymes in the consumer's body in a manner which reduces the deleterious effects of glucose on the consumer. The glucose reducing component can comprise at least one of a glucose oxidase enzyme and a glucose dehydrogenase enzyme. In another embodiment, the sweetener additive can have an alcohol reducing component that is selected to supplement naturally occurring enzymes in the consumer's body in a manner which reduces the deleterious effects of alcohol on the consumer. The alcohol reducing component can comprise at least one of an alcohol dehydrogenase enzyme and an alcohol oxidase enzyme. In yet another embodiment, the new sweetener additive can comprise various combinations of an aldehyde reducing component, a glucose reducing component and/or an alcohol reducing component that are selected to reduce aldehydes, glucose and/or alcohol in the body of the consumer so as to reduce or eliminate the deleterious effects thereof on the consumer.

Accordingly, the primary object of the present invention is to provide a new and improved sweetener additive that has the advantages set forth above and which overcome the known disadvantages and limitations that are associated with presently available sweeteners utilized with consumable products.

It is an important object of the present invention to provide a new sweetener additive that is configured to improve the health and well-being of the person who consumes a consumable product having the sweetener additive of the present invention.

It is also an important objective of the present invention to provide a new sweetener additive that, when a person consumes the sweetener additive with a consumable product, is able to stimulate naturally occurring enzymes in the person's body to more effectively process the sweetener by converting the ethanol and glucose associated with the consumable product in his or her bloodstream prior to being released and stored in the body.

It is also an important objective of the present invention to provide a new sweetener additive for use with a consumable product that, in addition to assisting in processing ethanol and glucose from the consumable product, is able to assist the body with the removal of other sugars and aldehydes in the person's body so as to reduce the negative effects thereof and improve the consumer's overall health and well-being.

An important aspect of the present invention is that it provides a new sweetener additive which accomplishes the various objectives set forth above and elsewhere in the present disclosure.

Another important aspect of the present invention is that it provides a new sweetener additive for use with consumable products, including a wide variety of foods and beverages, which promotes improved health and well-being of a person consuming the consumable product by stimulating the person's body to more effectively process, convert and remove ethanol, glucose and aldehydes in his or her body.

Another important aspect of the present invention is that it provides a new sweetener additive that is configured for use with producing or consuming a consumable product which is able to stimulate and supplement naturally occurring enzymes in the body of a person who consumes the consumable product to enable his or her body to more effectively process the sweetener by converting the ethanol and glucose associated with the consumable product prior to being released and stored in the body.

Another important aspect of the present invention is that it provides a new sweetener additive which is configured for use with producing or consuming a consumable product that is able to stimulate and supplement naturally occurring enzymes in the body of a person who consumes the consumable product to enable his or her body to more effectively process ethanol and glucose in the person's bloodstream and to process aldehydes, including acetaldehyde, in the person's bloodstream, whether the aldehydes are from consuming alcohol, environment, smoking, sugar consumption or other reasons.

Another important aspect of the present invention is that it provides a new sweetener additive which comprises a sweetener base and one or more flavonoids that are selected from the group consisting of Apigenin, Flavanones, Kaempferol, Quercetin, Rutin, Myricetin, Dihdrokaempferol, Dihydromyricetin, Ampelopsin, Epigallocatechin gallate and Taxifolin, which flavonoids may be from plants in the plant genus *Hovenia*, to stimulate naturally occurring enzymes in the body of a person who consumes a consumable product having the sweetener additive to more effectively convert ethanol, glucose and aldehydes in his or her bloodstream for improved health and well-being.

Another important aspect of the present invention is that it provides a new sweetener additive which has one or more flavonoids that are selected from the group consisting of Apigenin, Flavanones, Kaempferol, Quercetin, Rutin, Myricetin, Dihdrokaempferol, Dihydromyricetin, Ampelopsin, Epigallocatechin gallate and Taxifolin, which flavonoids are selected to stimulate and supplement naturally occurring enzymes in the body of a person who consumes a consumable product with the sweetener additive to help reduce the negative effects associated with hangover symptoms that result from consuming too much alcohol and the other deleterious effects of having an excess amount of aldehydes, including acetaldehyde, in the person's bloodstream.

Yet another important aspect of the present invention is that it provides a new sweetener additive for use with a consumable product which is adaptable for use with a wide variety of consumable products, easy to add to a consumable product during the production or consumption thereof and relatively inexpensive to manufacture.

As will be explained in greater detail by reference to the attached figures and the description of the preferred embodiments which follow, the above and other objects and aspects are accomplished or provided by the present invention. As set forth herein and will be readily appreciated by persons who are skilled in the art, the present invention resides in the novel features of form, construction, mode of operation and combination of processes presently described and understood by the claims. The description of the invention which follows is presented for purposes of illustrating one or more of the preferred embodiments of the present invention and is not intended to be exhaustive or limiting of the invention. The scope of the invention is only limited by the claims which follow after the discussion.

BRIEF DESCRIPTION OF THE DRAWINGS

In the drawings which illustrate the preferred embodiments and the best modes presently contemplated for carrying out the present invention.

DETAILED DESCRIPTION OF THE PREFERRED EMBODIMENTS

Figure 1:
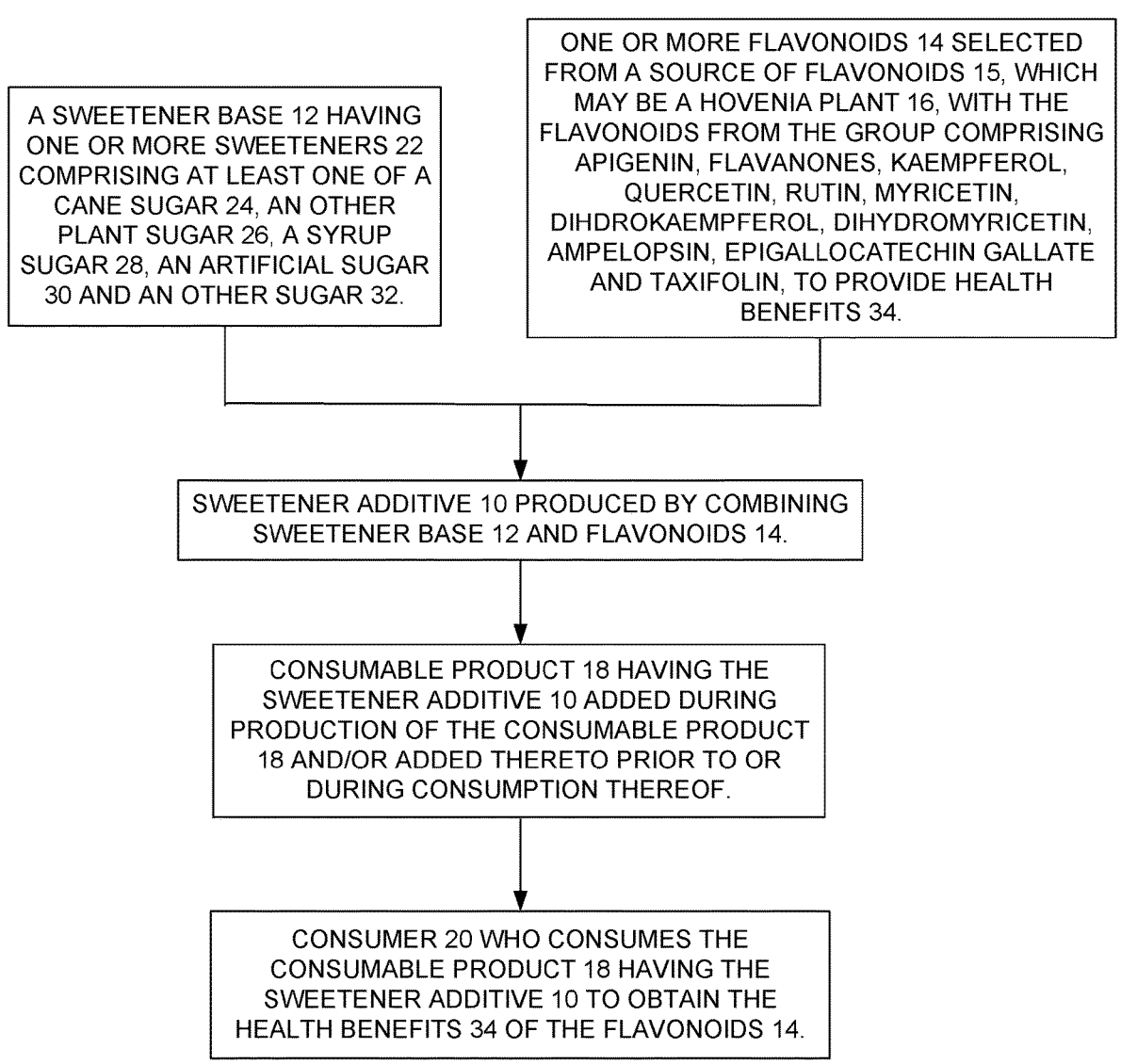
FIG. 1 is a chart showing the components that make up a sweetener additive that is configured according to a first embodiment of the present invention with one or more flavonoids selected from a group of flavonoids.

With reference to the figures where like elements have been given like numerical designations to facilitate the reader's understanding of the present invention, the preferred embodiments of the present invention are set forth below. The enclosed figures are illustrative of several potential preferred embodiments and, therefore, are included to represent several different ways of configuring the present invention. Although specific components, materials, configurations and uses are illustrated, it should be understood that a number of variations to the components and to the configuration of those components described herein and shown in the accompanying figures can be made without changing the scope and function of the invention set forth herein. For instance, although the description and figures included herewith generally describe and show particular materials and configurations for the new sweetener additive, persons who are skilled in the art will readily appreciate that the present invention is not so limited. In addition, the exemplary embodiments of the present device are shown and described with only those components which are required to disclose the present invention. Many of the necessary components for manufacturing or using the present invention are not shown in the drawings or necessarily described below, but which are well known to persons who are skilled in the relevant art. As will be readily appreciated by such persons, the various elements of the present invention that are described below may take on any form consistent with forms which are readily realized by one of ordinary skill in the art having knowledge of sweeteners utilized in the production or consumption of consumable products. In addition the new sweetener additive of the present invention can be provided in a wide variety of different flavors, colors and/or other configurations.

Figure 2:
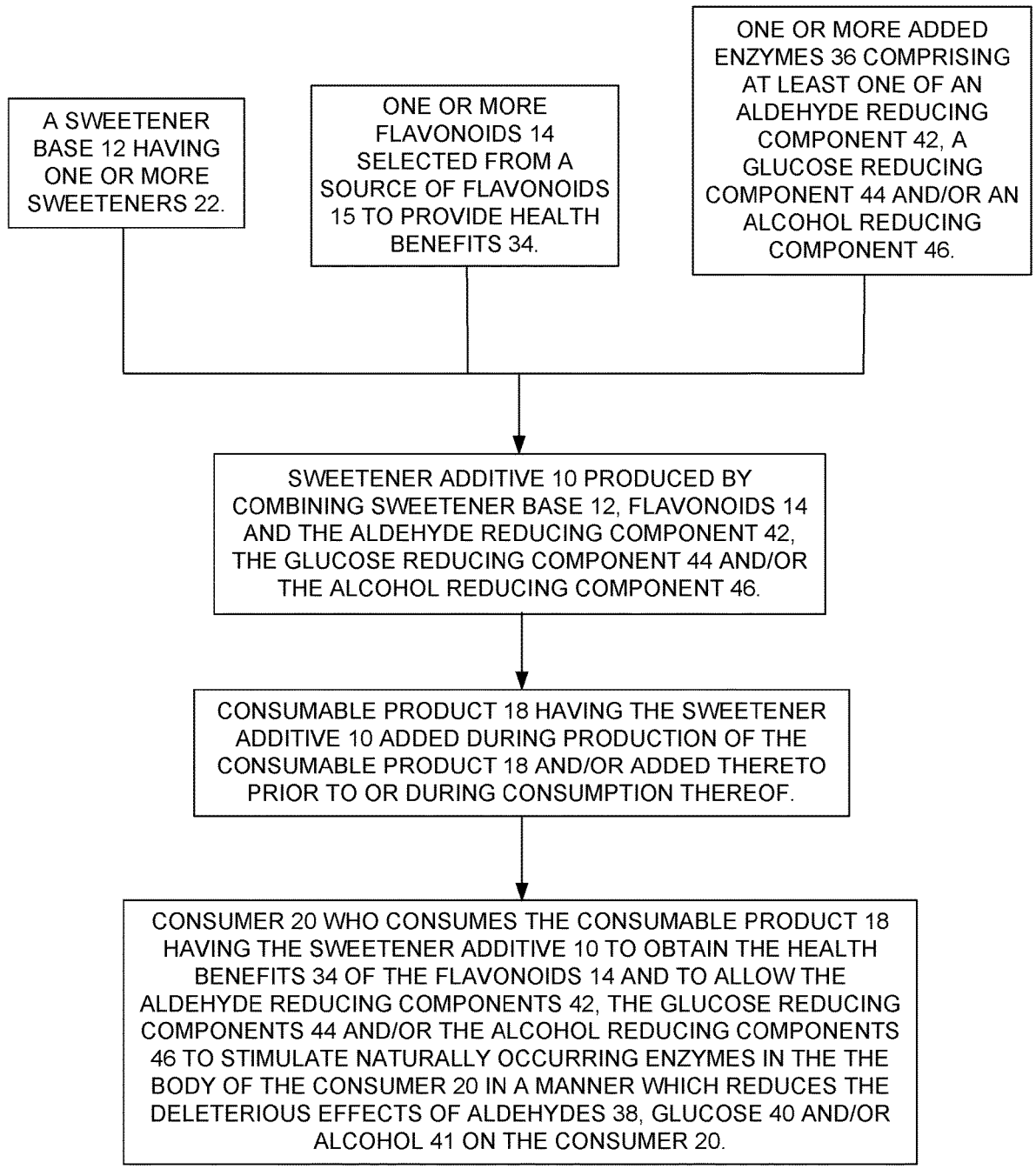
FIG. 2 is a chart showing the components that make of a sweetener additive that is configured according to a second embodiment of the present invention showing use of one or more of an aldehyde reducing component, a glucose reducing component and an alcohol reducing component.

A new sweetener additive that is configured pursuant to one or more of the preferred embodiments of the present invention is shown generally as 10 in FIGS. 1-2. As set in more detail below, in one basic embodiment of the present invention, the new sweetener additive 10 comprises a sweetener base 12 and a flavonoid 14 that is derived from a source of flavonoids 15, which may be plants in the plant genus *Hovenia* (hereinafter, plants that are from the plant genus *Hovenia* are collectively referred to as a *Hovenia* plant 16) that are combined, as may be appropriate for the sweetener base 12 and the flavonoid 14, together to form a unified, mixed sweetener additive 10. The sweetener additive 10 is configured to be mixed with a consumable product 18 such that a person (as a consumer 20) who consumes the consumable product 18 will consume the sweetener additive 10 and, most importantly, the flavonoids 14 from a *Hovenia* plant 16, that is mixed with the sweetener base 12. The consumable product 18 can be any type of food or beverage product that the consumer 20 can eat or drink. In addition, as set forth above and in more detail below, the new sweetener additive 10 can be added to the consumable product 18 during the production (i.e, baking, frying, freezing, mixing and etc.) of the consumable product 18, such as using the sweetener additive 10 as part of a recipe to make the consumable product 18 (commercially or privately) or the new sweetener additive 10 can be added to, such as being sprinkled on, spread over, mixed with or the like, by the consumer 20 or someone on his or her behalf (such as a parent or caretaker). More specifically, the new sweetener additive 10 of the present invention is likely to be able to be utilized in exactly the same manner and, at least generally, in the same quantities as if the sweetener base 12 was being utilized by itself for or with the consumable product 18. As described below, the sweetener base 12 typically functions as a stand-alone sweetener for use with producing and/or consuming consumable products 16 without utilization of the flavonoid 14 in the new sweetener base 12.

The sweetener base 12 for the sweetener additive 10 comprises one or more sweeteners 22 that may be natural, artificial or combinations of natural and artificial components, as shown in FIG. 1. One common type of sweetener 22 that is suitable for use as the sweetener base 12 for the sweetener additive 10 are collectively referred to, for purposes of describing the present invention, as "cane sugars" 24. One type of cane sugar 24 is referred to as granulated sugar, which is a highly refined white sugar that is made from beets or sugarcane. Granulated sugar is also referred to as table sugar, white sugar, refined sugar, beet sugar or cane sugar. Another cane sugar 24 is referred to as raw sugar, which is a cane sugar that is produced by evaporating the juice of pressed sugar cane and then separating the sugar crystals. As well known in the art, raw sugar is an umbrella term which includes any type of cane sugar 24 that is minimally refined and retains some of the molasses coating on the crystals. Raw sugars include, but are not limited to, such sugars as secant, rapadura, panela, muscovado, turbinado, and demarara sugar. Secant is a non-crystallized form of cane sugar that is made by extracting the juice of the sugar cane and then heating it until it forms a syrup, which is then cooled until sugar granules are formed. Secant has a grainy texture, rather than a crystalline texture, and is very dark as it retains a few of the original nutrients. Rapadura is a non-crystallized form of cane sugar 24 that is made by extracting the juice of the sugar cane and then heating it until it forms a syrup. The syrup is then cooled until the sugar granules are formed. Like secant sugar, rapadura has a grainy, rather than crystalline, texture and is very dark as it retains a few of the original nutrients. Rapadura and secant are probably the least processed of all the sugars derived from sugar cane. Panela sugar, also called raspadura or rapadura sugar, is also a minimally processed cane sugar 24 that is made by cooking the juice of pressed sugar cane. Muscovado, also referred to as barbados sugar, has a strong tasting flavor, brown color and is a moist and somewhat sticky cane sugar that is made from the first stage of crystallization. Because muscovado sugar is less processed than standard white sugar, this sugar retains more of the vitamins and minerals of the sugar cane. Turbinado sugar, also referred to as turbinated sugar, is a cane sugar 24 having large, light brown crystals that is produced by crushing sugar cane and collecting the juice, which is then evaporated and spun in a centrifuge (or turbine). This sweetener is less processed than white sugar. The names turbinado sugar and demerara sugar are often used interchangeably. Demerara sugar is another minimally processed cane sugar that is made by steaming the juice of pressed sugar cane to form a thick syrup. The syrup is allowed to dehydrate resulting in large, golden to medium brown crystals that are slightly sticky and have a unique flavor and texture. This sweetener is less processed and lower in calories than white sugar.

Confectioner's sugar, which is also referred to as powdered sugar, icing sugar and 10× sugar, is a highly refined cane sugar 24 that is made from beets or sugar canes that has been mechanically ground to produce a super fine, powdery sugar. Evaporated cane juice (also called dried cane juice, crystallized cane juice, cane crystals, cane juice crystals and milled cane sugar) is a refined cane sugar 24 made from sugar cane that retains some of the nutrients of the sugar cane. Evaporated cane juice is available in a variety of forms and under different names. This sweetener is slightly less processed than white sugar. Brown sugar is highly refined white sugar combined with varying amounts of molasses to yield golden, light, or dark brown sugar. Cane sugar 24 also includes fructose, glucose, sucrose and galactose, which are refined sugars which are made from sugar canes or sugar beets. Table sugar, which is refined white sugar, is made up of equal amounts of the simple sugars glucose and fructose, which are joined together by chemical bonds. Galactose is a refined sweetener that is found in a number of commercially prepared products. A galactose molecule linked with a glucose molecule forms a lactose molecule.

Another category of sweeteners 22 that are suitable for use as the sweetener base 12 for the sweetener additive 10 are collectively referred to herein as "other plant sugars" 26. One such other plant sugar 26 is referred to as beet sugar, which is a white sugar that is derived from beets. This sweetener is highly refined and has no nutrient value. Many people believe that beet sugar produces products with an inferior taste and texture compared to those made with cane sugar. Corn syrup is another type of other plant sugar 26. This thick, sweet syrup is made by heating corn starch with an acid or by combining it with enzymes to break it down. As such, corn sugar is a highly refined sweetener and has almost no nutritional value. Corn syrup solids, also called dried glucose syrup or glucose syrup solids, is corn syrup that has been concentrated to contain less than 10% water. Crystalline fructose is a sweetener produced by allowing the fructose from fructose-enriched corn syrup to crystallize. Agave is an other plant sugar 26 that is commercially produced from several species of the agave plant. Agave has more concentrated fructose than does high fructose corn syrup and has been shown to alter liver function, promote obesity, and increase insulin resistance for both diabetics and non-diabetics. Barley malt, which is also referred to as malt sweetener, is an other plant sugar 26 with a strong, distinctive flavor that is made from sprouted barley. Pure malt extract, which is relatively expensive, is often mixed with corn syrup, a less expensive product. Coconut sugar is produced from the sap of coconut flower buds (not the coconut itself). The sap is boiled to reduce moisture content and then dehydrated. There are concerns about the sustainability of producing coconut sugar due to the fact that coconut trees which are tapped for sap cannot produce coconuts. Date sugar, which is not really a refined sugar at all, is simply ground dates. This natural sweetener is high in fiber and nutrients and is considered to be a much better option than refined sweeteners. Date sugar can be used in place of sugar in some recipes. However, date sugar will not melt or dissolve in liquids as regular sugar does. Dextrose is a highly refined crystalline glucose that is made from starch. Dextrose produced from cornstarch may be listed as "corn sugar", that produced from rice may read as "rice sugar", and that made from wheat may be listed as "wheat sugar".

Honey and juice concentrate are also other plant sugars 26. Honey, which is a sweetener made by bees from plant nectar, contains trace amounts of vitamins and minerals. The color and flavor of the honey depends on the source of the nectar (clover, buckwheat, orange blossom, etc.). Another type of syrup sugar 28 is juice concentrate, which is a sweetener that is made by concentrating fruit juice. Juice concentrate typically retains a small amount of nutrients and is preferable to many other types of sweeteners when sweetening fruit-based dishes. In one example, grape juice concentrate is combined with rice syrup to produce a sweetener. Maltodextrins is a family of highly-refined sweeteners that are made from rice, corn, or potato starch. Maltose, also called malt sugar, is a sweetener that is made from malted grains. Mannitol is a sugar alcohol that is, unfortunately, known to cause digestive problems in some people. Maple syrup is a concentrated natural sweetener that is made by boiling down sap from the sugar maple tree.

Another category of sweeteners 22 that are suitable for use as the sweetener base 12 for the sweetener additive 10 are collectively referred to herein as "syrup sugars" 28. One syrup sugar 28 is high-fructose corn syrup (HFCS), which is a syrup made from corn that has undergone enzymatic processing to convert some of its glucose into fructose. Molasses, also called treacle, is a thick, dark syrup that is a by-product of the production of beet sugar or cane sugar 24. Sorghum syrup, which is sometimes called molasses, is a different product produced in a different way. Sorghum syrup, commonly referred to as sorghum molasses is a syrup that is made by crushing the stalks of the sorghum plant and then cooking the resulting syrup to concentrate it. In general, sorghum syrup is a more healthful option than regular or blackstrap molasses, which is a type of molasses. Blackstrap molasses is a thick, viscous, dark-colored syrup with a bittersweet flavor that is a waste product from processing sugar cane or beet into table sugar. Brown rice syrup is a thick, syrupy sweetener which is made by cooking brown rice flour or brown rice starch with enzymes. Some people believe brown rice contributes to the development of *candida* (yeast) more than any other type of sweetener 22.

Another category of sweeteners 22 that are suitable for use as the sweetener base 12 for the sweetener additive 10 are collectively referred to herein as "artificial sugars" 30. One example of an artificial sugar 30 is acesulfame potassium (acesulfame-K), which is also called Sunett®, a registered trademark of the Celanese Corporation. This artificial sugar 30 is a potassium salt containing methylene chloride, a known carcinogen. Long term exposure to methylene chloride can cause headaches, nausea, emotional imbalances, and damage to the liver and kidneys. Another artificial sugar 30 is acesulfame, which has been shown to produce breast tumors, lung tumors, and other types of tumors, leukemia, and chronic respiratory disease in rodents. The artificial sugar 30 aspartame, which is known by a variety of brand names, is an artificial sweetener that is comprised of approximately 50% phenylalanine, 40% aspartic acid, and 10% methanol and which is approximately 200 times sweeter than sugar. Reported side effects from the use of aspartame include abdominal pain, anxiety, arthritis, depression, headaches, fibromyalgia, memory loss, nausea, heart palpitations, irritable bowel syndrome, seizures, neurological disorders, vision problems, and weight gain. This artificial sugar 30 has also been shown to damage bacteria in the gut.

Yet another category of sweeteners 22 that are suitable for use as the sweetener base 12 for the sweetener additive 10 are collectively referred to herein as "other sugars" 32. For purposes of the present invention, other sugars include, but are not limited to, lactose, Sorbitol and Xylitol. As well known, lactose is the sugar that is found naturally in dairy products. It is usually the main factor responsible for milk intolerance. Sorbitol and Xylitol are alcohol sugars that, unfortunately, can cause digestion problems for some people.

As set forth above and shown in FIGS. 1-2, the sweetener additive 10 of the present invention comprises a quantity of sweetener base 12 that is mixed or otherwise combined with a quantity of one or more flavonoids 14 derived from a *Hovenia* plant 16. The new sweetener base 12 can comprise any one or more sweeteners 22, including without limitation the sweeteners 22 set forth above as cane sugar 24, other plant sugars 26, syrup sugars 28, artificial sugars 30 and other sugars 32. As will be readily appreciated by persons who are skilled in the art, however, the sweeteners 22 listed above are not exclusive to the sweeteners 22 that can be utilized as the sweetener base 12 for the sweetener additive 10 of the present invention. More specifically, the sweeteners 22 listed as cane sugar 24, other plant sugars 26, syrup sugars 28, artificial sugars 30 and other sugars 32 may include other types of sweeteners 22 within the subject categories as well as sweeteners 22 that do not fit in any of these categories. In general, any sweetener 22 for the sweetener base 12 is selected to be able to provide the desired benefits to the consumable product 18 that are normally are the reasons such sweeteners 22 are selected, which are usually to improve the taste of the consumable product 18. The sweetener 22 may also be selected to provide various health, consistency, color and/or other benefits for the consumable product 18.

As set forth above, the new sweetener additive 10 of the present invention also comprises a quantity of one or more flavonoids 14 that are selected from a source of flavonoids 15. As shown in FIG. 1, the flavonoids 14 for the sweetener additive 10 may be one or more flavonoids 14 that are selected from a group comprising Apigenin, Flavanones, Kaempferol, Quercetin, Rutin, Myricetin, Dihdrokaempferol, Dihydromyricetin, Ampelopsin, Epigallocatechin gallate and Taxifolin. The source of flavonoids 15 may be any source that can provide the desired flavonoids 14, whether they are obtained from organic sources, such plants, or they are produced in a laboratory or the like. In one embodiment, the flavonoids 14 are derived from plants in the plant genus *Hovenia*, namely the *Hovenia* plant 16, as shown in FIGS. 1-2. *Hovenia* is a small genus of deciduous trees or shrubs in the family Rhamnaceae, which is a large family of flowering plants, mostly trees, shrubs and some vines. Such plants occur naturally from India to Japan. Perhaps the best known species of these is the Japanese, or Oriental, raisin tree, which species is known as *Hovenia dulcis*, that is found throughout Asia. Although the tree bears edible fruit and is utilized as an ornamental tree, the raisin tree is best known for its health benefits when the leaves of the tree are consumed as a tea.

A wide variety of flavonoids can be extracted from the *Hovenia* plant 16 and utilized as the flavonoids 14 for the sweetener additive 10 of the present invention. More specifically, as set forth above and shown in FIGS. 1-2, flavonoids 14 which are extracted from plants in the plant genus *Hovenia* (*Hovenia* plant 16) can be mixed with one or more sweeteners 22 to produce the sweetener additive 10 that can be utilized in the production of and/or with the consumption of a consumable product 18. As set forth in more detail below, when a consumer 20 consumes a consumable product 18 having or combined with the new sweetener additive 10, the flavonoids 14 in the new sweetener additive 10 will provide certain health benefits 34, including stimulating naturally occurring enzymes in the body of a consumer 20, for him or her that will make consuming the consumable product 18 both enjoyable, due to the added sweetener 22 in the sweetener base 12, and much healthier, due to the flavonoids 14. The various flavonoids 14 that can be utilized with the sweetener additive 10 contribute a number of different, sometimes overlapping, health benefits 34. For purposes of describing the attributes and benefits of the sweetener additive 10 of the present invention, all such health benefits from the flavonoids 14 are herein collectively referred to as health benefits 34, regardless of the type of physiological or psychological benefit the flavonoids 14 provide to the consumer 18.

As set forth in FIGS. 1 and 2, the flavonoids 14 that are selected from the source of flavonoids 15, whether or not from a *Hovenia* plant 16, are selected to be utilized in the new sweetener additive 10 in order to provide health benefits 34. As set forth below, certain health benefits 34 have been identified with the flavonoids 14 for use with the present invention, which as set forth above include Apigenin, Flavanones, Kaempferol, Quercetin, Rutin, Myricetin, Dihdrokaempferol, Dihydromyricetin, Ampelopsin, Epigallocatechin gallate and Taxifolin, as shown in FIG. 1. These flavonoids 14, whether from the *Hovenia* plant 16 or another source of flavonoids 15, have been studied and identified as having health benefits 34. For instance, Apigenin is a common dietary flavonoid that is abundantly present in many fruits, vegetables and Chinese medicinal herbs that provide health benefits 34 which provide multiple physiological functions for a consumer 18, including but not limited to strong anti-inflammatory, antioxidant, antibacterial and antiviral activities and blood pressure reduction. The flavonoid Flavanones have health benefits that include strong antioxidant and radical scavenging activity, reduced risks of certain chronic diseases and the prevention of some cardiovascular disorders and certain types of cancer. The flavonoid Kaempferol reduces the risk of chronic diseases, especially cancer. In addition, Kaempferol augments the human body's antioxidant defense against free radicals, modulates apoptosis, angiogenesis, inflammation, and metastasis. The flavonoid Quercetin has antioxidant and anti-inflammatory effects which are believe to help reduce inflammation, kill cancer cells, control blood sugar and help prevent heart disease. The flavonoid Rutin helps strengthen and increase flexibility in blood vessels, such as arteries and capillaries, which can improve the consumer's overall health. In addition, Rutin is likely to help ease related conditions, including bruises, spider veins and varicose veins. The flavonoid Myricetin has the health benefit 34 of ameliorating insulin resistance and functions for anti-oxidative stress, anti-inflammation, anti-aldose reductase, anti-non-enzymatic glycation and anti-hyperlipidemia. All of these functions may provide the contribution to the prevention of diabetic complications. The flavonoid Dihydrokaempferol is believed to provide potential health benefits 34 due to its antioxidant properties. The flavonoid Dihydromyricetin (also known as DHM) has been demonstrated to have antioxidative, anti-inflammatory, anticancer, antimicrobial, cell death-mediating, and lipid and glucose metabolism-regulatory health benefits 34. The flavonoid dihydromyricetin is also shown to be able to reduce aldehyde, including acetaldehyde, in the body of the consumer 18. Dihydromyricetin exhibits health benefit activities with minimum adverse effects. Ampelopsin, also called dihydromyricetin, is a natural flavonoid (also found in the Chinese herb *Ampelopsis grossedentata*), that possess multiple pharmacological functions including anti-inflammatory, anti-oxidative and anti-cancer functions. The flavonoid Epigallocatechin gallate (also referred to as EGCG) is a unique plant compound is thought to have the health benefits 34 of being able to reduce inflammation, aid weight loss, and help prevent heart and brain disease. The flavonoid Taxifolin has also been shown to provide benefits to cardiovascular health, the pores and skin, cognitive feature, contamination, allergic reactions and immunodeficiency, in addition to the fitness of diabetics. However, the primary benefit of Taxifolin is its antioxidant efficiency and vascular-defensive movement. As will be readily appreciated by persons who are skilled in the art, the above-described flavonoids 14 can be utilized separately or more than one of the flavonoids 14 (or all) can be combined together with a sweetener base 12 for the sweetener additive 10 such that a sweetener additive 10 having any one or more of the above-identified flavonoids 14 are within the intended scope of the sweetener additive 10 of the present invention.

People skilled in the art will readily appreciate that the flavonoids 14 set forth above are not the only flavonoids 14 that may be derived from the *Hovenia* plant 16 and that the health benefits 34 which are described above as being associated with those flavonoids 14 are not likely to be the only health benefits 34 that can benefit the consumer 18. More specifically, additional research into the *Hovenia* plant 16 is likely to result in the identification of additional flavonoids 14 that can be utilized with the sweetener additive 10 to provide one or more health benefits 34. Likewise, additional research and study into the above flavonoids 14, as well as any future identified flavonoids 14 from the source of flavonoid 14, including from the *Hovenia* plant 16, is likely to identify other health benefits 34 that can benefit the consumer 16 who consumes a consumable product 18 having or with the sweetener additive 10.

As set forth in U.S. patent application Ser. No. 16/998, 933, which has the same inventor as the present patent application, the use of the flavonoid dihydromyricetin (DCM) in a chewing gum to reduce aldehyde accumulation in the body of the consumer 18, whether such accumulation is from the consumption of alcohol, or from pollution, smoking, vaping and/or poor eating habits and/or for consumers 18 whose body, for physiological or genetic reasons, do not naturally process aldehydes very well. The full and complete disclosure set forth in U.S. patent application Ser. No. 16/998,933 is hereby incorporated into the present text as though fully set forth herein.

As described above and shown on FIGS. 1 and 2, the new sweetener additive 10 can be utilized in the production of a consumable product 18 or it can be utilized with the consumption of a consumable product 18, either of which are consumed by the consumer 18 to achieve the health benefits 34 of the sweetener additive 10. The consumable product 18 can be virtually any food or beverage product, including meat, vegetable, fruit and other meals and beverages such as sodas, juices, alcohol, alcohol mixes, exercise drinks, diet drinks and the like. The new sweetener additive 10 can be provided in liquid, granulated, solid or other forms and directly incorporated into a consumable product 18, into a mix (such as powdered drink, gravy, sauce and like mixes) and/or be utilized by itself in place of sugar or artificial sweeteners that can be directly added to a drink such as coffee, tea and the like. In one use of the sweetener additive 10, the sweetener additive 10 is utilized by the manufacturer or other producer of a food or beverage product in the production of the consumable product 18 by using the sweetener additive 10 in place of or in addition to the sweetener 22 that the manufacturer or producer normally utilizes when producing the consumable product 18. In another use, the sweetener additive 10 is added to a consumable product 18 by the consumer 20, or someone on his or her behalf, prior to or while consuming the consumable product 18 to improve or enhance the flavor of the consumable product 18. In either use, the addition of the sweetener additive 10 of the present invention in place of or in addition to one or more other sweeteners 22 will also provide the consumer 20 with the health benefits 34 that are associated with the flavonoids 14 that are included in the sweetener additive 10, which includes those described above and stimulating naturally occurring enzymes in the consumer's body (all of which are health benefits 34). For purposes of manufacturing and using the sweetener additive 10 of the present invention, the are virtually no limits as to the type, use and/or configuration of the consumable product 18 and to how or when (i.e., what stage of completion or consumption) the sweetener additive 10 is added to the consumable product 18.

The consumer 20 of the consumable product 18 having the sweetener additive 10 or to which the sweetener additive 10 is added can be any person who may benefit from the health benefits 34 resulting from combining one or more flavonoids 14 with sweetener base 12. Although not fully studied, it is anticipated that the sweetener additive 10 of the present invention may also be beneficial to animals, particularly dogs, cats and other pets, as the consumer 18 thereof.

In a second embodiment of the present invention, shown in FIG. 2, the new sweetener additive 10 also has, in addition to the flavonoids 14, one or more added enzymes 36 that are specially selected to supplement naturally occurring enzymes in the consumer's body in order to reduce the amount of aldehyde 38, glucose 40 and/or alcohol 41 in the bloodstream of a consumer 18 who consumes a consumable product 18 having the sweetener additive 10 therein or added thereto. The added enzymes 36 in the sweetener additive 10 can comprise at least one aldehyde reducing component 42, at least one glucose reducing component 44 and/or at least one alcohol reducing component 46 that are selected such that when a consumer 20 consumes a consumable product 18, the added enzymes 36 will be absorbed into the consumer's body to reduce the amount of aldehyde 38, glucose 40 and/or alcohol 41 in his or her body. As will be readily appreciated by persons who are skilled in the art, the inclusion of the added enzymes 36 will provide further health benefits 34, as set forth herein, to the consumer 20 of a consumable product 18 having the sweetener additive 10.

In one embodiment, the aldehyde reducing component 42 of the new sweetener additive 10 comprises an aldehyde dehydrogenase enzyme. In another embodiment, the glucose reducing component 44 of the sweetener additive 10 comprises a glucose oxidase enzyme and/or a glucose dehydrogenase enzyme. In another embodiment, the alcohol reducing component 46 of the new sweetener additive 10 comprises an alcohol dehydrogenase enzyme and/or an alcohol oxidase enzyme. In yet another embodiment, the new sweetener additive 10 comprises combinations of two or more of the aldehyde reducing component 42, the glucose reducing component 44 and the alcohol reducing component 46 such that the sweetener additive 10 has at least one of the alcohol dehydrogenase enzyme, the glucose oxidase enzyme and the glucose dehydrogenase enzyme, and/or the aldehyde dehydrogenase enzyme and the alcohol oxidase enzyme. In any of these configurations, the sweetener additive 10 will be able to provide the health benefits 34 described above (from the flavonoids 14) and the additional health benefits 34 from further reducing the levels of aldehydes 38 and/or glucose 40 in the body of a consumer 20 who consumes a consumable product 18 having the new sweetener additive 10. The added enzymes 36 will supplement the naturally occurring enzymes in the body of the consumer 20 and the flavonoids will stimulate both the added enzymes 36 and the naturally occurring enzymes.

Utilizing the sweetener additive 10 with the addition of the aldehyde reducing component 42, glucose reducing component 44 and/or alcohol reducing component 46 with the flavonoids 14 will help safely and effectively remove aldehyde 38, glucose 40 and/or alcohol 41 from the bloodstream of a consumer when he or she consumes a consumable product 18 having the new sweetener additive 10. More specifically, once a consumer 20 consumes the consumable product 18, the digestive process of his or her body will result in the aldehyde reducing components 42, glucose removing components 44 and/or the alcohol reducing components 46 being absorbed into his or her bloodstream through the stomach and other internal organs. As well known in the art, the additive enzymes 36 will start working on the consumable product 18 in the stomach as soon as it is consumed and continue working on the glucose 40 and alcohol 41 components of the consumable product 18 as they work their way through the digestive process of the consumer 20, thereby converting the various glucose 40 and alcohol 41 (as ethanol) components before the small intestine directs these components into the bloodstream. With regard to the aldehyde reducing component 42, once absorbed into the person's bloodstream, the aldehyde reducing components 42 will react with the aldehyde 38 in the person's bloodstream to remove or at least lower the amount of aldehyde 38 in his or her body, including that added by the reduction of the glucose 40 and alcohol 41, thereby preventing or reducing the harmful effects of a buildup of aldehyde 38 in the consumer's body. Likewise, once absorbed into the person's bloodstream, the glucose reducing components 44 will react with glucose 40 in the person's bloodstream to remove or at least lower the amount of glucose 40 in his or her body, which will prevent or reduce the harmful effects of a buildup of glucose 40. The alcohol reducing component 46 will help convert the ethanol from the alcohol 41 to lessen the likelihood of the alcohol 41 entering the consumer's bloodstream.

As well known in the art, the build-up of aldehyde 38, often in the form of acetaldehyde, in a consumer's body can result from the consumption of alcohol. Not only is acetaldehyde a known carcinogen, its toxic effects are a well known cause of many of the side effects of consuming alcohol, particularly an alcohol hangover (as set forth in the Background). Removing acetaldehyde from the person's bloodstream is known to reduce hangover symptoms. When the ability of a person's body's to oxidize acetaldehyde to acetate is inhibited, typically either chemically or due to genetics for certain persons, amplified hangover symptoms are common. In addition to aldehyde 38 being introduced into a person's bloodstream by alcohol, aldehyde 34 is known to enter a person's bloodstream as a result of exposure to a number of chemicals that are or can be found in the environment, workplace and other locations where a person may frequent and due to smoking, vaping and/or poor eating habits. As set forth in more detail below, the new sweetener additive 10 of the present invention is safe and effective at removing aldehydes 38, including but not limited to acetaldehyde, from a person's bloodstream, no matter how it may enter the consumer's bloodstream.

In the sweetener additive 10 of the present invention acetaldehyde and other aldehydes 38 are removed from a person's bloodstream by the inclusion of the aldehyde dehydrogenase enzyme into the sweetener additive 10. More specifically, in one embodiment of the present invention, the sweetener additive 10 comprises a therapeutically effective amount of the aldehyde dehydrogenase enzyme. For purposes of describing the sweetener additive 10, a therapeutically effective amount is that amount of aldehyde dehydrogenase which is necessary, desired or beneficial to interact with the aldehyde 38 in a person's bloodstream to lower the level of aldehyde 38, which may be in the bloodstream due to the consumption of food, beverages and/or alcohol 41 or from other sources (as set forth above), to a level which is safe and which provides the various benefits that are sought by use of the sweetener additive 10 of the present invention, including as applicable prevention or reduction of hangover symptoms. As will be readily appreciated by persons who are skilled in the art, the aldehyde dehydrogenase enzyme can be incorporated into sweetener additive 10 in a variety of different manners, whether directly or as a part of compounds containing the enzyme.

Likewise, glucose 40 is removed from a person's bloodstream by the inclusion of the glucose oxidase enzyme and/or glucose dehydrogenase enzyme into the sweetener additive 10. More specifically, in one embodiment of the present invention, the sweetener additive 10 comprises a therapeutically effective amount of glucose oxidase. In another embodiment, the new sweetener additive has a therapeutically effective amount of glucose dehydrogenase. In yet another embodiment, the new sweetener additive 10 has a therapeutically effective amount of both glucose oxidase and glucose dehydrogenase. For purposes of describing sweetener additive 10, a therapeutically effective amount is that amount of glucose oxidase and/or glucose dehydrogenase which is necessary, desired or beneficial to interact with glucose 40 in a person's bloodstream to lower the level of glucose 40 in his or her body. As will be readily appreciated by persons who are skilled in the art, the glucose oxidase and glucose dehydrogenase enzymes can be incorporated into sweetener additive 10 in a variety of different manners, whether directly or as part of compounds that contain these enzymes.

Likewise, alcohol 41 (as ethanol) is removed from the bloodstream of a consumer 20 by the inclusion of the alcohol dehydrogenase enzyme and/or the alcohol oxidase enzyme into the sweetener additive 10. More specifically, in one embodiment of the present invention, the sweetener additive 10 comprises a therapeutically effective amount of the alcohol dehydrogenase enzyme. In another embodiment, the new sweetener additive 10 has a therapeutically effective amount of the alcohol oxidase enzyme glucose dehydrogenase. In other embodiments, the new sweetener additive 10 has a therapeutically effective amount of both and/or a therapeutically effective amount of alcohol dehydrogenase enzyme and the alcohol oxidase enzyme. For purposes of describing the new sweetener additive 10, a therapeutically effective amount is that amount of alcohol dehydrogenase and/or alcohol oxidase which is necessary, desired or beneficial to interact with alcohol 41 in a person's bloodstream to lower the level of alcohol 41 in his or her body. As will be readily appreciated by persons who are skilled in the art, the one or more alcohol dehydrogenase and/or alcohol oxidase enzymes can be incorporated into the new sweetener additive 10 in a variety of different manners, whether directly or as part of compounds that contain these enzymes.

As set forth above, the new sweetener additive 10 comprises the sweetener base 12 and one or more flavonoids 14 that are selected from a source of flavonoids 15, which may be a *Hovenia* plant 16. The flavonoids are selected from the group comprising at least one of Apigenin, Flavanones, Kaempferol, Quercetin, Rutin, Myricetin, Dihdrokaempferol, Dihydromyricetin, Ampelopsin, Epigallocatechin gallate and Taxifolin. The sweetener base 12 is made up of one or more sweeteners 22. The quantity and type of flavonoids 14 in the sweetener additive 10 are selected to achieve general or specific health benefit 34 objectives. The sweetener additive 10 of the present invention is generally utilized in the same manner as the sweeteners 22 would be utilized, namely the sweetener additive 10 is included in a consumable product 18 during the manufacturing or production thereof and/or added to a consumable product 18 prior to or before consuming the consumable product 18. In contrast to prior art sweeteners 22, the new sweetener additive 10 will provide health benefits 34 to the consumer 20 consuming the consumable product 18. Specifically, as set forth in more detail above, the flavonoids 14 included in the new sweetener additive 10 of the present invention will provide a wide variety of health benefits 34 depending on the types and amounts of flavonoids 14 in the sweetener additive 10, including stimulating the naturally occurring enzymes in the consumer's body that remove aldehyde 38, glucose 40 and/or alcohol 41. The addition of the added enzymes 36, namely, the aldehyde reducing components 42, the glucose reducing components 44 and/or the alcohol reducing components 46 to the flavonoids 14 in a sweetener additive 10 that is incorporated in or utilized with a consumable product 18 provide the additional health benefit 34 of further reducing aldehyde 38, glucose 40 and/or alcohol 41 in the consumer's body by supplementing the naturally occurring enzymes in his or her body to further improve the health of the consumer 20 who consumes the consumable product 18. The action of the added enzymes 36 will also be stimulated by the flavonoids 14.

As will be readily appreciated by persons who are skilled in the relevant art, the amount of flavonoids 14 and the amount of aldehyde reducing components 42, glucose reducing components 44 and/or alcohol reducing components 46 in the sweetener additive 10 can be adjusted to achieve one or more health related objectives that are to be achieved by consuming a consumable product 18 having the sweetener additive 10. For instance, such persons will readily understand that if a slower/lesser or faster/increased metabolization of aldehyde 38, glucose 40 and/or alcohol 41 is desired or necessary, then the concentrations of the aldehyde reducing components 42, glucose reducing components 44 and/or alcohol reducing components 46 in the sweetener additive should be adjusted accordingly to determine the therapeutically effective amount that will provide the desired beneficial effect. When consumed, the new sweetener additive 10 will aid in improving the general health of a consumer 20 who consumes a consumable product 18 having the sweetener additive 10 and, if the aldehyde reducing components 42, glucose reducing components 44 and/or alcohol reducing components 46 are utilized in the sweetener additive 10, will supplement naturally occurring enzymes to further help those consumers 20 who have problems with the build-up of aldehydes 38 from eating food and/or drinking beverages, including alcohol 41, or who are exposed to aldehydes 38 as a result of pollution, smoking, vaping and/or poor eating habits and/or for persons whose body, for physiological or genetic reasons, do not naturally process aldehydes 38 very well and for persons for whom glucose 40 and/or alcohol 41 are a problem.

While there are shown and described herein specific forms of the invention, it will be readily apparent to those skilled in the art that the invention is not so limited, but is susceptible to various modifications and rearrangements in design and materials without departing from the spirit and scope of the invention. For instance, there may be numerous components of the embodiments described herein that can be readily replaced with equivalent functioning components to accomplish the objectives and obtain the desired aspects of the present invention. The various embodiments set forth herein are intended to explain the best mode of making and using the present invention as currently known to and appreciated by the present inventor and to enable other persons who are skilled in the relevant art to make and utilize the present invention. Although, the described embodiments may comprise different features, not all of these features are required in each and every embodiment of the present invention. More specifically, as will be readily appreciated by persons who are skilled in the art, certain embodiments of the present invention only utilize some of the features and/or combinations of features disclosed herein.

What is claimed is:

1. A sweetener additive for a consumable product to improve health and well-being of a consumer of the consumable product, wherein said sweetener additive comprises:
    a sweetener base having one or more sweeteners; and
    one or more flavonoids combined with said sweetener base, said one or more flavonoids extracted from a source of flavonoids to provide one or more health benefits for the consumer who consumes the consumable product having said sweetener additive, said one or more flavonoids selected from the group comprising at least one of apigenin, flavanones, kaempferol, quercetin, rutin, myricetin, dihdrokaempferol, dihydromyricetin, ampelopsin, epigallocatechin gallate and taxifolin,
    wherein said sweetener additive is configured to be added to the consumable product during production of the consumable product and/or after production of the consumable product but before the consumer eats or drinks the consumable product.

2. The sweetener additive of claim 1, wherein said source of flavonoids is a *hovenia* plant.

3. The sweetener additive of claim 1, wherein said one or more sweeteners of said sweetener base comprises at least one of a cane sugar, an other plant sugar, a syrup sugar, an artificial sugar and an other sugar.

4. The sweetener additive of claim 1 further comprising an aldehyde reducing component that is selected to supplement naturally occurring enzymes in the consumer's body in a manner which reduces deleterious effects of aldehydes on the consumer.

5. The sweetener additive of claim 4, wherein said aldehyde reducing component comprises an aldehyde dehydrogenase enzyme.

6. The sweetener additive of claim 1 further comprising a glucose reducing component that is selected to supplement naturally occurring enzymes in the consumer's body in a manner which reduces deleterious effects of glucose on the consumer.

7. The sweetener additive of claim 1, wherein said sweetener additive is prepared according to a method comprising the steps of:
    (a) providing said source of flavonoids;
    (b) extracting said one or more flavonoids from said source of flavonoids;
    (c) providing said sweetener base; and (d) combining said one or more flavonoids with said sweetener base.

8. The sweetener additive of claim 6 further comprising an aldehyde reducing component that is selected to stimulate naturally occurring enzymes in the consumer's body in a manner which reduces deleterious effects of aldehydes on the consumer.

9. The sweetener additive of claim 1 further comprising an alcohol reducing component that is selected to convert and consume alcohol in the consumer's body in a manner which reduces deleterious effects of alcohol on the consumer.

10. The sweetener additive of claim 9, wherein said alcohol reducing component comprises at least one of an alcohol dehydrogenase enzyme and an alcohol oxidase enzyme.

11. The sweetener additive of claim 9 further comprising an aldehyde reducing component that is selected to stimulate naturally occurring enzymes in the consumer's body in a manner which reduces deleterious effects of aldehydes on the consumer.

12. A sweetener additive for a consumable product to improve health and well-being of a consumer of the consumable product, wherein said sweetener additive comprises:
   a sweetener base having one or more sweeteners, said one or more sweeteners being at least one of a cane sugar, an other plant sugar, a syrup sugar, an artificial sugar and an other sugar;
   one or more flavonoids combined with said sweetener base, said one or more flavonoids extracted from a source of flavonoids to provide one or more health benefits for the consumer who consumes the consumable product having said sweetener additive, said one or more flavonoids selected from the group comprising at least one of apigenin, flavanones, kaempferol, quercetin, rutin, myricetin, dihdrokaempferol, dihydromyricetin, ampelopsin, epigallocatechin gallate and taxifolin; and
   an aldehyde reducing component that is selected to stimulate naturally occurring enzymes in the consumer's body in a manner which reduces deleterious effects of aldehydes on the consumer,
   wherein said sweetener additive is configured to be added to the consumable product during production of the consumable product and/or after production of the consumable product but before the consumer eats or drinks the consumable product.

13. The sweetener additive of claim 12, wherein said source of flavonoids is a *hovenia* plant.

14. The sweetener additive of claim 12, wherein said aldehyde reducing component comprises at least one of an alcohol dehydrogenase enzyme and an aldehyde dehydrogenase enzyme.

15. The sweetener additive of claim 12 further comprising a glucose reducing component that is selected to stimulate naturally occurring enzymes in the consumer's body in a manner which reduces the deleterious effects of glucose on the consumer.

16. The sweetener additive of claim 12, wherein said sweetener additive is prepared according to a method comprising the steps of:
   (a) providing said source of flavonoids;
   (b) extracting said one or more flavonoids from said source of flavonoids;
   (c) providing said sweetener base;
   (d) providing said aldehyde reducing component; and
   (d) combining said one or more flavonoids and said aldehyde reducing component with said sweetener base.

17. The sweetener additive of claim 12 further comprising an alcohol reducing component that is selected to convert and consume alcohol in the consumer's body in a manner which reduces deleterious effects of alcohol on the consumer.

18. The sweetener additive of claim 17, wherein said alcohol reducing component comprises at least one of an alcohol dehydrogenase enzyme and an alcohol oxidase enzyme.

19. A method of making a sweetener additive for a consumable product to improve health and well-being of a consumer of the consumable product, wherein said method comprises the steps of:
   (a) providing a source of flavonoids;
   (b) extracting one or more flavonoids from said source of flavonoids, said one or more flavonoids selected from the group comprising at least one of apigenin, flavanones, kaempferol, quercetin, rutin, myricetin, dihdrokaempferol, dihydromyricetin, ampelopsin, epigallocatechin gallate and taxifolin;
   (c) providing a sweetener base having one or more sweeteners; and
   (d) combining said one or more flavonoids with said sweetener base to produce said sweetener additive.

20. The method of claim 19, wherein said sweetener additive is configured to be added to the consumable product during production of the consumable product and/or after production of the consumable product but before the consumer eats or drinks the consumable product.

* * * * *